United States Patent [19]
Carlson

[11] Patent Number: 5,674,256
[45] Date of Patent: Oct. 7, 1997

[54] CARDIAC PRE-EJECTION PERIOD DETECTION

[75] Inventor: Gerrard M. Carlson, Champlin, Minn.

[73] Assignee: Cardiac Pacemakers, Inc., St. Paul, Minn.

[21] Appl. No.: 574,674

[22] Filed: Dec. 19, 1995

[51] Int. Cl.$^6$ .................................................. A61N 1/365
[52] U.S. Cl. .................................................. 607/17
[58] Field of Search .................................. 607/17, 19, 24, 607/25

[56] References Cited

U.S. PATENT DOCUMENTS

| | | |
|---|---|---|
| 4,719,921 | 1/1988 | Chirife . |
| 4,730,619 | 3/1988 | Koning et al. . |
| 4,773,401 | 9/1988 | Citak et al. . |
| 4,865,036 | 9/1989 | Chirife . |
| 5,156,142 | 10/1992 | Warren et al. ............... 607/24 |
| 5,549,650 | 8/1996 | Boronz et al. ............... 607/25 |

*Primary Examiner*—William E. Kamm
*Attorney, Agent, or Firm*—Haugen And Nikolai, P.A.

[57] ABSTRACT

A method of and apparatus for controlling a rate adaptive pacer is disclosed which operates based on the pre-ejection period (PEP), the method including the step of detecting the pre-ejection period utilizing only the pacer ECG signal and an accelerometer transducer signal.

8 Claims, 2 Drawing Sheets

CARDIAC PRE-EJECTION PERIOD DETECTION

BACKGROUND OF THE INVENTION

I. Field of the Invention

The present invention relates generally to cardiac pacing systems in which the pacing rate responds to varying physiological or metabolic needs and, more particularly, to rate adaptive pacing of the type responsive to changes in the ventricular pre-ejection period (PEP). The invention focuses on an improved cardiac pre-ejection period method and detector (CPEPD) system for use in rate adaptive pacing which measures the pre-ejection period based on processed accelerometer signals in combination with detected R-wave and signal energy gated time of minimum error to regulate the pulsing or pacing rate. The invention is useful in bradycardia, tachycardia and congestive heart failure therapy devices.

II. Related Art

Workers in the cardiac pacing field have long recognized the desirability of creating an implantable device capable of maintaining an adequate heart rate in a patient suffering from bradycardia at a nominal level with the individual at rest but which would also automatically adapt to changes in metabolic need to increase the pacing rate above that baseline value.

The patent literature is replete with rate adaptive pacemaker designs in which a wide variety of physiologic parameters are sensed as an indicator of metabolic need and used to develop a pacing rate control signal for a rate adaptive pacemaker. There also are defibrillation devices which make use of some of these parameters.

Among these, pacing or defibrillation devices have been proposed that have made use of the measurement or monitoring of the pre-ejection period of the heart. One such device for effecting cardioversion or defibrillation that monitors the pre-ejection period to sense whether an increase in heart rate is accompanied by a decrease in the pre-ejection period to indicate the presence of a physiological rather than pathological reason for heart rate increase, i.e., whether cardioversion is indicated, is disclosed by Raul Chirife in U.S. Pat. No. 4,865,036. In U.S. Pat. No. 4,719,921, also to Chirife, there is described a pacing system in which the left ventricular pre-ejection period is measured and converted to an electrical signal with such electrical signal being used to control the rate of a cardiac pacemaker. In the Chirife application, the pre-ejection period or PEP is defined as the period beginning with the QRS complex (R-wave) and ending with the onset of ventricular ejection which is measured based on pressure equalization with the aorta diastolic pressure. It is explained that the PEP varies predictably in response to the release of catecholamines into the blood and with direct sympathetic nerve activity when physiologic demands increase.

Citak et al (U.S. Pat. No. 4,773,401) use a sensing lead to measure instantaneous impedance in the right ventricle and signal process the resulting impedance waveform to extract a time interval in keeping with a paced beat or spontaneous QRS complex until the impedance versus time signal crosses the zero axis or at a predetermined point in the positive going waveform. This time interval is used to control a rate responsive pacer.

Since the pre-ejection period (PEP) shortens in response to systemic factors, such as sympathetic time, that also govern the contractibility of the myocardium, it also shortens in response to increased demand for cardiac output during exercise increased activity and emotional stress. To deal effectively with this aspect of pacing, a less complicated use of PEP including a more accurate PEP sensing system would be desirable in adaptive rate pacing.

Accordingly, it is a principal object of the present invention to provide an improved device for extracting PEP for application in pacemakers pacing control and congestive heart failure therapy devices.

Another object of the invention is to provide an apparatus that provides a beat-by-beat determination of PEP by means of an autoregressive model based inverse filtering of accelerometer signals with QRS or R-wave and signal energy gated time of minimum error detection.

Other objects and advantages of the invention will become apparent to those skilled in the art in connection with the materials contained in the present specification.

SUMMARY OF THE INVENTION

The present invention provides an improved method of cardiac pre-ejection period detection (CPEPD) together with an improved (CPEPD) system which is useful in bradycardia, tachycardia and congestive heart failure therapy devices. The CPEPD invention utilizes an accelerometer signal such as, for example, a transducer signal from a subcutaneous pectoral located accelerometer in conjunction with an endocardial ECG signal provided by a heart pacer to provide the necessary input information for PEP detection. The particular placement of the accelerometer sensor is not critical and other placement locations may be used, as well.

The system measures the PEP of the current beat as the time difference between the peak of the QRS or "R" wave of the ECG signal which gives rise to ejection during the then-current beat and a time defined as the time of minimum prediction error or the time of best autoregressive (AR) match of the accelerometer trace to that of a predetermined model accelerometer transducer signal evaluated during baseline conditions. The time of best AR match is confined to a time window that begins relative to the then-current "R" wave, which gives rise to ejection during the then-current beat, and ends on the trailing edge of the main lobe of the energy signal. This is depicted in trace D of FIG. 1. The system of the invention further refines the allowed time of best match to fall within that window and also within the main lobe of the energy signal of the accelerometer during the then-current beat.

In the preferred embodiment and method, a preconditioned version of the accelerometer signal is processed by Levinson or the Yule-Walker algorithm from autocorrelation lags of the accelerometer signal derived during the time of the main lobe of the energy signal. The resulting reflection coefficients describing the reference signal are utilized in an inverse filter, the output of which is scaled by the running RMS estimate of the accelerometer signal during the main lobe of the energy signal. This output is fed to a peak detector whose output indicates the time of the peak absolute value of the scaled inverse filter output. This time corresponds to the time of minimum prediction error or the best AR match. The time of the current R wave is subtracted from the time of best AR match to obtain PEP.

The preferred implementation of the inverse filter is that of a finite impulse response (FIR) lattice filter as this implementation results in a structure that is maximally numerically stable. Once the coefficient parameters for the inverse FIR lattice filter are determined during baseline conditions, the beat-by-beat determination of PEP from accelerometer measurements can be used as a control input to a rate adaptive pacemaker.

BRIEF DESCRIPTION OF THE DRAWINGS

In the drawings wherein like numerals depict like parts throughout the same.

DETAILED DESCRIPTION

The pre-ejection period used for adaptive rate pacing control in accordance with the invention includes both recognized subdivisions, i.e., the electromechanical interval and the isovolumic contraction time. The present cardiac pre-ejection period detector (CPEPD) invention measures the pre-ejection period (PEP) of the current beat as the time difference between the peak of the QRS or "R" wave of the ECG signal which gives rise to ejection during the then-current beat and a time defined as the time of minimum prediction error or the time of best autoregressive (AR) match of an accelerometer transducer signal to that of a predetermined model. The time of best AR match is limited to a time window that begins with the current "R" wave, which gives rise to ejection during the current beat, and ends on the trailing edge of the main lobe of the energy signal (FIG. 1).

Figure 1:
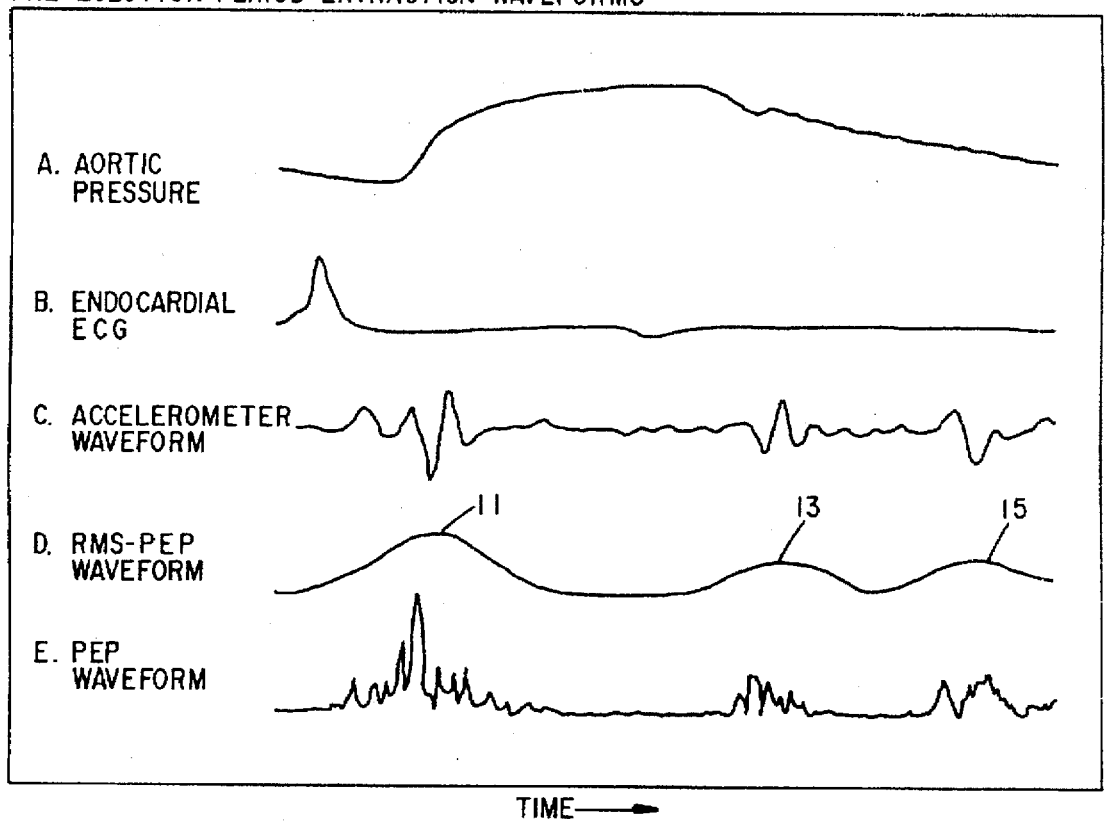
FIG. 1 depicts a plurality of synchronized time traces in a series of plots A-E including aortic pressure, endocardial (ECG), accelerometer waveform, RMS-PEP waveform and the PEP waveform.

The traces of FIG. 1 at A and B depict the aortic pressure and endocardial ECG signal. Trace C is a plot of the accelerometer waveform showing its relation in time to the aortic pressure and endocardial ECG traces. The traces for D (RMS-PEP waveform) and E (PEP waveform) are signals derived during the processing of the other signals in the signal processing pipeline flow diagram illustrated in FIG. 2. The trace of FIG. 1D representing the RMS-PEP energy waveform may be characterized as having a primary or main lobe of the energy signal 11, secondary lobe 13 and tertiary lobe 15.

Figure 2:
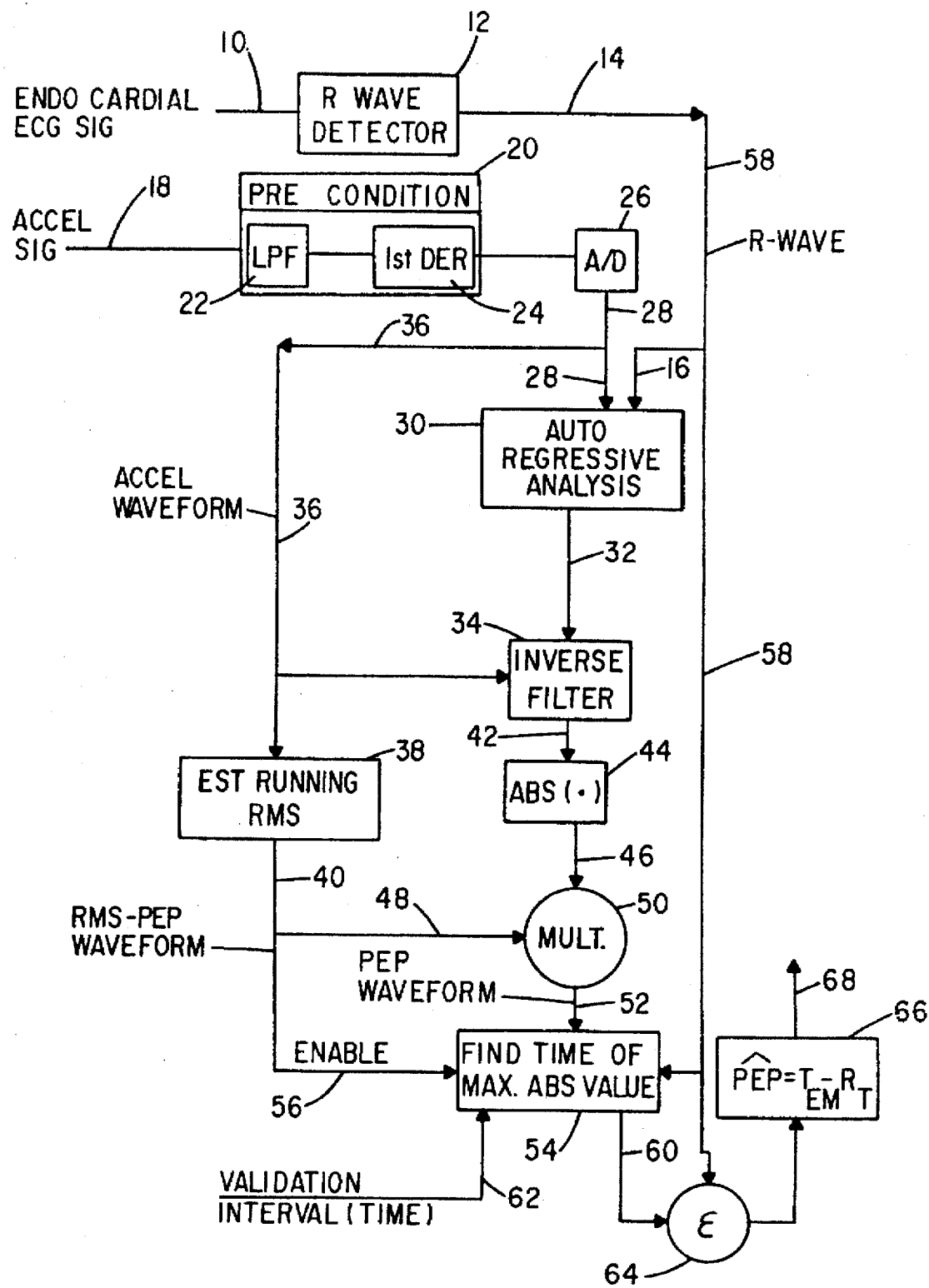
FIG. 2 depicts the signal processing pipeline of the invention.

FIG. 2 depicts the signal processing pipeline of the invention in flow-chart form. The pipeline operates to extract PEP using autoregressive signal analysis of a pre-conditioned accelerometer signal in conjunction with time of peak residual extraction. As can be seen in FIG. 2, an input from the ECG signal available from the pacemaker to be controlled on line 10 is subjected to an R-wave detector 12 which extracts and generates a number on line 14 indicative of the time of the R-wave. This signal is also present on lines 58 and 16.

The signal processing pipeline of the present invention enables PEP to be extracted using only accelerometer sensor signals and electrocardiogram (ECG) signals which are available from the pacer. The accelerometer may be mounted in the pacer itself or on the body surface or subcutaneously where it senses fluid acceleration or cardiac tissue acceleration indicative of the onset of ejection. Those devices and their placement and operation are well known.

The accelerometer signal processing pipeline of the invention uses several fixed or reference parameters with respect to processing the accelerometer signals. An accelerometer transducer signal on line 18 is evaluated during baseline conditions, i.e., with the wearer at rest. One method of preconditioning the signal is shown at 20 and includes a low pass filter 22 and a pre-emphasis signal processor 24 which extracts the first derivative of the low pass filter signal.

The first derivative of the low pass filter signal is then digitized by an A-to-D converter at 26. Precondition steps 22-26 enhance the pre-ejection accelerometer signature portion of the signal that is due to the on-set of ejection and further filter out other events which are extraneous to the desired control parameters. In this manner, the bandwidth of the signal is limited by eliminating non-essential frequencies utilizing the low pass filter and the higher frequency components within the remaining band width are enhanced.

The preconditioned version of the accelerometer signal on line 28 is processed at 30 by auto-regressive analysis using well-known Levinson or the Yule-Walker algorithms from autocorrelation lags of the accelerometer signal derived during the time of the main lobe of the energy signal. A discrete set of reflection coefficients describing the reference signal result. This coefficient set is fed on line 32 for use as an input to an inverse linear filter predictor at 34.

A segment of the preconditioned/digitized accelerometer data generated on line 36 is subjected to a square root RMS data extraction at 38, the output of which is the smoothed RMS-PEP waveform of trace 1D of FIG. 1 on line 40. At this point, this segment of the raw complex wave packet of the accelerometer output signal has been preconditioned and is smoothed and activity not related to the timing component has been removed or filtered out. The inverse linear predictor filter produces an output indicative of the intensity or ongoing intensity energy level of the accelerometer signal as a function of time.

In the inverse linear predictor filter, the signal is subjected to an autoregressive process by a linear prediction operation such that the time of relevant minimum error becomes a positive spike in the output. The time of maximum absolute value of the spike corresponds to the time of minimum error with respect to the beginning of ejection. The output generates a larger response when the input signal matches the same preconditioned signal parameter fixed for the filter 34. The inverse filter output on line 42 is changed to an absolute value parameter at 44 so that the maximum value of the spike can be determined and the output on line 46 is scaled by the running RMS estimate of the accelerometer signal on line 48 during the main lobe of the energy signal in the multiplier 50.

The preferred implementation of the inverse filter is that of an FIR lattice filter. This implementation results in a structure that is maximally numerically stable, since stable filters result in coefficient multiplication operations that are bounded in absolute value by 1. Further, it turns that the meaningful coefficient values corresponding to the relatively few "taps" needed are usually greater than 0.5 in absolute value, making this embodiment preferred where integer math is to be used.

Having determined the coefficient parameters for the inverse FIR lattice filter, the beat-by-beat determination of PEP is made using real time accelerometer measurements. The absolute value of the output of the inverse filter is sealed by the running RMS value of the accelerometer signal in real time at 50 on line 52 and is fed to a peak detector 52, whose output on line 60 is the time of the peak absolute value of the scaled inverse filter output signal.

The peak detector 54 is enabled on line 56 during a validation interval or a time window that begins relative to the then-current R wave and ends on the trailing edge of the main lobe of the energy signal on line 58 based on a signal on line 62.

The time of the then-current "R" wave on line 58 is differenced from the time of best AR match on line 60 by subtraction at 64 to obtain a PÊP output at box 66. The PÊP output signal is available to any devices desired to be used as shown on line 68. The signal values on lines 60 and 58 are integers and so the output of the output of the difference of them at 64 (PÊP output) is also represented by an integer. In this manner, one measurement is determined for each peak.

The time of the peak absolute value of the scaled inverse filter output corresponds to the time of minimum prediction error or best match described above. This is because the AR model best interprets an observed signal as a system impulse response. The interval of time corresponding to the minimum prediction error also defines the time of the hypothetical impulse that gave rise to the waveform under consideration. A maximum in the scaled inverse filter output is sought since this maximum in the residual output corresponds to the impulse that gave rise to the observed event.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

I claim:

1. A method of determining the pre-ejection period (PEP) for use in controlling a rate adaptive pacer based on the PEP measured during an on-going cardiac beat and using accelerometer sensor signals and electrocardiogram (ECG) signals, the method comprising the steps of
    (a) providing an accelerometer trace signal of cardiac activity;
    (b) detecting the peak of the R wave of the ECG signal; and
    (c) measuring the PEP of an on-going cardiac beat as the time difference between the peak of the R wave of the ECG signal which gives rise to ejection during said on-going cardiac beat and a time defined as the time of minimum prediction error which is the time of best autoregressive (AR) match of the accelerometer trace to that of a predetermined model accelerometer transducer signal evaluated during baseline conditions.

2. The method of claim 1 wherein an allowable time to determine the time of best AR match is confined to a time window that begins with the peak of the R wave, which gives rise to ejection during said on-going cardiac beat, and ends with the end of a main lobe of the RMS-PEP waveform corresponding to said beat.

3. The method of claim 1 further comprising the steps of:
    (a) preconditioning the accelerometer signal;
    (b) processing a first segment of the preconditioned accelerometer signal of (a) by algorithms selected from the group consisting of Levinson and Yule-Walker from autocorrelation lags of the accelerometer signal derived during the time of a main lobe of the RMS-PEP waveform;
    (c) subjecting the output of the processed signal of (b) to an inverse filter;
    (d) extracting the output of the inverse filter as an absolute value;
    (e) processing a second segment of the preconditioned accelerometer signal of (a) to produce a running RMS estimate of the accelerometer signal;
    (f) scaling the absolute value of the output of the inverse filter by the running RMS estimate of the accelerometer signal during the main lobe of the RMS-PEP waveform to produce a scaled signal;
    (g) using a peak detector to detect the peak absolute value of the scaled signal in (f) to determine the time of minimum prediction error, which is the time of best AR match; and
    (h) subtracting the time of the R wave peak from the time of best AR match to obtain PEP.

4. The method of claim 3 wherein the step of subjecting the output of the processed signal of (b) to an inverse filter includes subjecting same to an FIR lattice filter.

5. The method of claim 3 wherein an allowable time to determine the time of best AR match is confined to a time window that begins with the peak of the R wave, which gives rise to ejection during said on-going cardiac beat, and ends with the end of a main lobe of the RMS-PEP waveform corresponding to said beat.

6. The method of claim 3 wherein the step of preconditioning the accelerometer signal further comprises the steps of
    (a) subjecting the accelerometer signal to a low pass filter;
    (b) extracting the first derrivative of the output of the low pass filter; and
    (c) digitizing the signal using an A-to-D converter.

7. In a cardiac pre-ejection period detector for use in controlling a rate adaptive pacer based on the pre-ejection period (PEP) said pacer having an ECG signal detector including an R wave peak detector means and an associated accelerometer transducer having an output signal:
    (a) means for preconditioning the accelerometer output signal;
    (b) means for processing a first segment of the preconditioned accelerometer output signal of (a) to produce a running RMS-PEP waveform of the accelerometer output signal;
    (c) means for processing a second segment of the preconditioned accelerometer output signal of (a) using algorithms selected from the group consisting of Levinson and Yule-Walker from autocorrelation lags of the accelerometer signal derived during the time of a main lobe of the RMS-PEP signal to produce an auto-regressive (AR) signal output;
    (d) inverse filter means for processing said AR signal output and producing an inverse filter output signal;
    (e) means for producing an absolute value signal from the inverse filter output signal;
    (f) multiplying means for scaling the absolute value of the output of the inverse filter by the running RMS-PEP waveform of the accelerometer signal during the main lobe of the RMS-PEP waveform;
    (g) detector means to detect the peak absolute value of the scaled inverse filter output signal to determine the time of minimum prediction error which is the best AR match; and
    (h) means for subtracting the time of the peak of the R wave from the time of the best AR match to obtain PEP.

8. The apparatus of claim 7 wherein said inverse filter is an FIR lattice filter.

* * * * *